United States Patent
Mejia et al.

(10) Patent No.: US 10,590,151 B2
(45) Date of Patent: Mar. 17, 2020

(54) SILANES AND CURABLE COMPOSITIONS COMPRISING SAID SILANES

(71) Applicant: Henkel AG & Co. KGaA, Duesseldorf (DE)

(72) Inventors: Esteban Mejia, Rostock (DE); Dengxu Wang, Rostock (DE); Udo Kragl, Kritzmow (DE); Andrea Gutacker, Duesseldorf (DE); Therese Hemery, Duesseldorf (DE); Adrian Duracu, Duesseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 16/296,361

(22) Filed: Mar. 8, 2019

(65) Prior Publication Data

US 2019/0202844 A1     Jul. 4, 2019

Related U.S. Application Data

(63) Continuation of application No. PCT/EP2017/072298, filed on Sep. 6, 2017.

(30) Foreign Application Priority Data

Sep. 13, 2016 (EP) .................................. 16188603

(51) Int. Cl.
| | |
|---|---|
| *C07F 7/18* | (2006.01) |
| *C08K 5/5419* | (2006.01) |
| *C08G 77/16* | (2006.01) |
| *C08G 77/18* | (2006.01) |

(52) U.S. Cl.
CPC ............ *C07F 7/188* (2013.01); *C07F 7/1804* (2013.01); *C08K 5/5419* (2013.01); *C08G 77/16* (2013.01); *C08G 77/18* (2013.01)

(58) Field of Classification Search
None
See application file for complete search history.

(56) References Cited

U.S. PATENT DOCUMENTS

| | | | |
|---|---|---|---|
| 4,552,942 A | 11/1985 | Kreuzer et al. | |
| 7,091,298 B2 | 8/2006 | Schindler et al. | |
| 8,569,439 B2 | 10/2013 | Ederer et al. | |
| 9,481,817 B2 | 11/2016 | Pichl et al. | |
| 2012/0016072 A1* | 1/2012 | Ederer ................ | C08K 5/5419 524/588 |

FOREIGN PATENT DOCUMENTS

| | | |
|---|---|---|
| CA | 2979929 A1 | 9/2016 |
| DE | 3210337 A1 | 9/1983 |
| EP | 0520426 A1 | 12/1992 |
| EP | 1230298 B1 | 7/2003 |
| EP | 2030976 A1 | 3/2009 |
| JP | 2011026498 A1 | 2/2011 |
| WO | 9933906 A1 | 7/1999 |
| WO | 03014226 A1 | 2/2003 |
| WO | 2005085356 A1 | 9/2005 |
| WO | 2006099054 A2 | 9/2006 |
| WO | 2009027103 A2 | 3/2009 |
| WO | 2013022532 A1 | 2/2013 |
| WO | 2014135261 A1 | 9/2014 |
| WO | 2016146648 A1 | 9/2016 |

OTHER PUBLICATIONS

International Search Report for International PCT Patent Application No. PCT/EP2017/072298 dated Nov. 20, 2017.
DIN 55672-1:Aug. 2007.
N. Huesing, P. Jakubiak, Monatshefte Fur Chemie 2006, 137, 635-645 (Synthesis of lactate silane).
A. D. Woolfson, R. K. Malcolm, S. P. Gorman, D. S. Jones, A.F. Brown and Stephen D. McCullagh, J. Mater. Chem., 2003, 13, 2465-2470 (Self-lubricating silicone biomaterials).
A. Berkefeld et al., Organometallics 2014, 33, 2721-2737 (Self-lubricating silicone biomaterials).
International Search Report for International PCT Patent Application No. PCT/EP2016/055620 dated Jun. 6, 2016.
M.M. Sprung in "Some α-Caraloxyalkoxy-silanes", J. Org. Chem., 1958, 23 (10), Seiten 1530-1534.
Wang et al., "B-Lactam-Forming Photochemical Reactions of . . . ", Journal of Organic Chemistry, vol. 69, 2004, pp. 1215-1220.
International Search Report for International PCT Patent Application No. PCT/EP2016/055693 dated Jun. 17, 2016.

* cited by examiner

*Primary Examiner* — Clinton A Brooks
*Assistant Examiner* — Kofi Adzamli
(74) *Attorney, Agent, or Firm* — James E. Piotrowski

(57) ABSTRACT

The invention relates to silane compounds having the general formula (I): $SiR^1{}_n(R^2)_{4-n}$ (I), as defined herein, to a method for preparing the silane compounds and use thereof as crosslinker or as adhesion promoter and to a curable composition comprising a reaction product of the at least one silane compound, at least one polyorganosiloxane, and at least one catalyst, and use thereof.

16 Claims, No Drawings

SILANES AND CURABLE COMPOSITIONS COMPRISING SAID SILANES

The present invention relates to new silanes which have malate esters, the preparation thereof, as well as crosslinkers comprising the silanes and curable compositions comprising the silanes and polyorganosiloxanes.

Silicone polymers (polyorganosiloxanes), particularly polydialkylsiloxanes such as polydimethylsiloxane (PDMS), have great importance in the production of adhesive, sealing, coating, spray foam, and insulation materials, which have been widely used in many fields such as construction, electronic, communication, aerospace, cosmetic and medicine, etc. Among these, those that vulcanize at low temperatures and under ambient conditions, so-called room temperature vulcanized (RTV) silicone rubber materials constitute a not insignificant share of the market. Typical formulations contain a reactive polyorganosiloxane, a crosslinker (or so-called hardener), catalyst, filler and others. As a rule, the reactive polyorganosiloxane is a silanol-terminated polyorganosiloxane, wherein the polyorganosiloxane has at least one, preferably two hydroxyl groups bound to a silicon atom and the crosslinker is a polyfunctional compound, commonly tri- and/or tetrafunctional compound, which is used to link the polysiloxane into the crosslinked networks. The term curing agent is also used occasionally instead of crosslinker. The polyorganosiloxane and crosslinker can be present as separate components. The polyorganosiloxane is often reacted selectively with the crosslinker, however, to form a modified polyorganosiloxane, and said modified polyorganosiloxane is added to the curable composition. The term endcapping (end group capping) is also used in this regard. This can be carried out optionally in the presence of a catalyst, whereby the catalyst is to mediate the endcapping selectively without simultaneously curing the polyorganosiloxane.

By adjusting the crosslinker amount and species, polymerization rate, chemical and physical properties of the resulting silicone rubber materials can be designed and tuned.

Numerous crosslinkers for silicone systems are known. The most frequently chosen crosslinkers are silane-based compounds containing hydrolyzable SiX groups, which condense with the Si—OH groups from polysiloxanes to form the crosslinked networks. These can be differentiated into acidic, basic, and neutral crosslinkers based on the leaving groups released during hydrolysis. Typical acidic crosslinkers contain hydrolizable carboxyl groups, e.g., acetate, and release the corresponding acids, e.g., acetic acid, during the crosslinking reaction. Typical basic crosslinkers release amines, e.g., hexylamine, during the crosslinking reaction. Typical representatives of neutral crosslinkers have hydrolyzable groups, which split off an alcohol, e.g., methanol or ethanol, or oxime, e.g., methyl-ethylketoxime during the crosslinking. These released compounds are commonly volatile organic compounds (VOCs), which have a high vapor pressure at ordinary room temperature leading to relatively large amounts of molecules released into the surrounding environment.

The VOCs released from silanes during crosslinking are commonly toxic and harmful for the environment, and human and animal organisms. For example, amines and acids released from aminosilanes and acetoxysilanes are severe irritants to the skin, eyes and mucous membranes, and they are also corrosive to metal, stone or mortar. Alcohols, especially methanol, released from commercially available alkoxysilanes, may cause humans with blurred vision, headache, dizziness and nausea after acute (short-term) or chronic (long-term) exposure. Oximes released from another commonly used oximosilanes, especially vinyltris(methylethylketoximino)silane, can cause serious eye irritation.

Moreover, all the silanes mentioned above are disadvantageous that the released VOCs during crosslinking have unpleasant or irritating odors, and sometimes smell extremely awful, resulting in great discomfort, especially when working with them in a closed space.

Silane compounds that release α-hydroxycaboxylic acid esters or α-hydroxycaboxylic acid amides, which have high boiling points and thus low volatility, during crosslinking, have already been proposed therefore as alternative crosslinkers.

The preparation of suitable silane compounds has been known for a long time and is described, for example, by M. M. Sprung in "Some α-carbalkoxyalkoxysilanes," *J. Org. Chem.*, 1958, 23 (10), 1530-1534.

DE 32 10 337 A1 as well discloses relevant silane compounds and the preparation and use thereof in curable compositions based on polydiorganosiloxanes, which have condensable end groups.

EP 2 030 976 A1 discloses a hardener for silicone rubber materials comprising a silane compound which comprises a 2-hydroxy-propionic acid alkyl ester radical, also called lactate esters. The released compounds, i.e., lactate esters, have higher boiling points than common released compounds, thus resulting in lower volatility. Especially ethyl ester (ethyl lactate) is an approved food additive, has a mild fruity scent and is harmless for the environment and human and animal organisms. Although lactate esters show lower volatility than common released compounds, they can still be discharged into the surrounding environment because of their relatively high vapor pressure (ethyl lactate: 1.163 mmHg/25° C.) and low boiling point (ethyl lactate: 152-154° C.).

Moreover, using silanes crosslinkers with low-volatility leaving groups may result in silicone rubber materials with some specific properties. Woolfson et al. describes silicone rubber elastomers exhibiting a persistent lubricous surface and coefficients of friction approaching zero using tetra (alkoxyl)silane, especially tetra(oleyloxyl)silane as crosslinkers, in which alcohols with long alkyl chain were released after crosslinking (A. D. Woolfson, R. K. Malcolm, S. P. Gorman, D. S. Jones, A. F. Brown and Stephen D. McCullagh, *J. Mater. Chem.*, 2003, 13, 2465-2470.). However, the melting points of these alcohols are relatively high (e.g., oleyl alcohol: 0-5° C.) and the alcohols may turn into solid from liquid on the surface of the silicone rubber materials in cold spaces, especially in winter, thereby limiting their application range.

Accordingly, a need still exists for the crosslinkers for curing silicone rubber materials which overcome the drawbacks of the above-mentioned silane-based crosslinkers.

The object of the present invention is therefore to provide a new silane compounds that can be used as neutral crosslinkers in curable compositions based on polyorganosiloxanes while maintaining acceptable crosslinking properties without influencing the storage of the curable compositions negatively.

It has been found that the object is achieved by introducing compounds with low volatility in the silanes as the hydrolyzable groups. To reduce the VOCs released from the system, silanes are required that release instead organic compounds with an extremely low volatility at ambient conditions.

The present invention therefore provides silane compounds of malate esters which can be used as crosslinkers in curable compositions based on polyorganosiloxanes. The released compounds, i.e., malate esters, during crosslinking have an extremely low volatility. Moreover, they are non-toxic and non-corrosive and have pleasant odours. Furthermore, diethyl malate and dibutyl malate are approved food additives.

The silanes of the present invention can be used as crosslinkers for curing silicone compositions and other polymers, adhesion promoters for adhesives and/or sealants, coupling agents for binding organic polymers to mineral or siliceous fillers, surface modifiers on different substrates, water scavengers, and dispersing agents. etc.

The present invention provides silane compounds having the general formula (I)

$$SiR^1_n(R^2)_{4-n} \quad (I)$$

wherein
each $R^1$ is same or different and is, independently of one another, selected from radicals having the general formula (II)

$$-OCH(CH_2COOR^3)COXR^3 \quad (II)$$

wherein X is O or N, and
each $R^3$ is same or different and is, independently of one another, selected from the group consisting of substituted or unsubstituted, linear or branched alkyl radicals having from 1 to 22 carbon atoms, aryl radicals having from 6 to 16 carbon atoms, and cycloalkyl radicals having from 5 to 27 carbon atoms, where $R^3$ may contain at least one heteroatom selected from O, N, S and/or Si;
each $R^2$ is same or different and is, independently of one another, selected from the group consisting of a hydrogen atom, a hydroxyl group, substituted or unsubstituted monovalent hydrocarbon radicals, preferably selected from alkenyl, alkyl, or aryl radicals, having from 1 to 18 carbon atoms, preferably from 1 to 8 carbon atoms, and alkoxy radicals having from 1 to 8 carbon atoms, preferably from 1 to 3 carbon atoms; and
n is 2, 3, or 4, preferably 3 or 4.

The present invention relates further to a method for preparing the silane compound of the present invention, crosslinkers comprising at least one silane compound of the invention, and use of the silane compound as a crosslinker for a curing silicone composition or as an adhesion promoter for adhesives or sealants.

The present invention relates further to curable compositions comprising at least one reaction product of at least one silane compound of the invention and at least one polyorganosiloxane having at least one hydroxyl group, vinyl group, or hydrogen atom bound to a silicone atom, and at least one catalyst and their use as adhesives, sealants, spray foam or coatings.

A "curable composition" is understood to be a substance or mixture of multiple substances, which is curable by physical or chemical measures. In this regard, these chemical or physical measures can be, for example, the supplying of energy in the form of heat, light, or other electromagnetic radiation, but also simply bringing into contact with atmospheric moisture, water, or a reactive component. The composition thereby changes from an original state to a state that has a higher hardness.

Provided reference is made to molecular weights of oligomers or polymers in the present application, the quantities, unless otherwise stated, refer to the weight average, i.e., the $M_w$ value, and not to the arithmetic average. The molecular weight is determined by gel permeation chromatography (GPC) with tetrahydrofuran (THF) as the eluent according to DIN 55672-1:2007-08, preferably at 35° C. Molecular weights of monomeric compounds are calculated based on the respective molecular formula and the known molecular weights of the individual atoms.

"At least one," as used herein, means 1 or more, i.e., 1, 2, 3, 4, 5, 6, 7, 8, 9, or more. With reference to an ingredient, the indication refers to the type of ingredient and not to the absolute number of molecules. "At least one polymer" thus means, for example, at least one type of polymer, i.e., that one type of polymer or a mixture of several different polymers may be used. Together with the weight indication, the indication refers to all compounds of the stated type which are contained in the composition/mixture, i.e., that the composition contains no further compounds of this type besides the stated quantity of the compounds in question.

The term "about", as used herein in connection with a numerical value, relates to a variance of ±20%, preferably ±10% of the respective value.

Unless explicitly stated otherwise, all percent values provided in conjunction with the compositions described herein refer to % by weight, in each case based on the mixture in question.

An "alkyl" group/radical, as used herein, refers to a saturated aliphatic hydrocarbon including linear and branched groups. The alkyl can be an intermediate alkyl, which has 5 to 6 carbon atoms, or a lower alkyl, which has 1 to 4 carbon atoms, e.g., methyl, ethyl, n-propyl, isopropyl, butyl, isobutyl, tert-butyl, etc. The alkyl groups can be substituted or unsubstituted. "Substituted," as used in this connection, means that one or more carbon atoms and/or hydrogen atom(s) of the alkyl group are replaced by heteroatoms or functional groups. Heteroalkyl groups in which one or more carbon atoms are replaced by heteroatoms, particularly selected from O, S, N, and/or Si, are obtained by the replacement of one or more carbon atoms by heteroatoms. Examples of such heteroalkyl groups are, without limitation, methoxymethyl, ethoxyethyl, propoxypropyl, methoxyethyl, isopentoxypropyl, ethylaminoethyl, trimethoxypropylsilyl, etc. Functional groups that can replace the hydrogen atoms are selected particularly from =O, =S, —OH, —SH, —NH$_2$—NO$_2$, —CN, —F, —Cl, —Br, —I, —OCN, —NCO, $C_{3-8}$ cycloalkyl, $C_{6-14}$ aryl, a 5-10-membered heteroaryl ring, in which 1 to 4 ring atoms independently are nitrogen, oxygen, or sulfur, and a 5-10-membered heteroalicyclic ring, in which 1 to 3 ring atoms are independently nitrogen, oxygen, or sulfur.

An "alkenyl", as used herein, refers to an alkenyl group/radical which consists of at least two carbon atoms and at least one carbon-carbon double bond, e.g., ethenyl, propenyl, butenyl, or pentenyl and structural isomers thereof such as 1- or 2-propenyl, 1-, 2-, or 3-butenyl, etc. Alkenyl groups can be substituted or unsubstituted. If they are substituted, the substituents are as defined above for alkyl.

An "alkynyl," as used herein, refers to an alkynyl group/radical which consists of at least two carbon atoms and at least one carbon-carbon triple bond, e.g., ethynyl (acetylene), propynyl, butynyl, or petynyl and structural isomers thereof as described above. Alkynyl groups can be substituted or unsubstituted. If they are substituted, the substituents are as defined above for alkyl.

A "cycloaliphatic" or "cycloalkyl" group/radical, as used herein, refers to monocyclic or polycyclic groups (a number of rings with carbon atoms in common), in which the ring does not have a completely conjugated pi-electron system, e.g., cyclopropyl, cyclobutyl, cyclopentyl, cyclohexyl, cyclobutenyl, cyclopentenyl, cyclohexenyl, etc. Cycloalkyl groups can be substituted or unsubstituted. "Substituted," as used in this regard, means that one or more hydrogen atoms of the cycloalkyl group are replaced by functional groups. Functional groups that can replace the hydrogen atoms are selected particularly from =O, =S, —OH, —SH, —NH$_2$, —NO$_2$, —CN, —F, —Cl, —Br, —I, —OCN, —NCO, C$_{1-10}$ alkyl, C$_{2-10}$ alkenyl, C$_{2-10}$ alkynyl, C$_{3-8}$ cycloalkyl, C$_{6-14}$ aryl, a 5-10-membered heteroaryl ring, in which 1 to 4 ring atoms independently are nitrogen, oxygen, or sulfur, and a, 5-10-membered heteroalicyclic ring, in which 1 to 3 ring atoms independently are nitrogen, oxygen, or sulfur.

An "aryl" group/radical, as used herein, refers to monocyclic or polycyclic groups (i.e., rings that have neighboring carbon atoms in common) which have a completely conjugated pi-electron system. Examples of aryl groups are phenyl, naphthalenyl, and anthracenyl. Aryl groups can be substituted or unsubstituted. If they are substituted, the substituents are as defined above for cycloalkyl.

Each R$^1$ in the general formula (I) is same or different and is, independently of one another, selected from radicals having the general formula (II)

—OCH(CH$_2$COOR$^3$)COXR$^3$    (II).

X in the general formula (II) is O or N, preferably O. Each R$^3$ in the general formula (II) is same or different and is, independently of one another, selected from the group consisting of substituted or unsubstituted, linear or branched alkyl radicals having from 1 to 22 carbon atoms, preferably from 1 to 8 carbon atoms, aryl radicals having from 6 to 16 carbon atoms, preferably from 6 to 10 carbon atoms, and cycloalkyl radicals having from 5 to 27 carbon atoms, preferably from 5 to 16 carbon atoms. R$^3$ may contain at least one heteroatom selected from O, N, S and/or Si. In preferred embodiments, R$^3$ is selected from linear or branched alkyl radicals having from 1 to 22 carbon atoms and cycloalkyl radicals having from 5 to 27 carbon atoms, more preferably selected from a methyl, ethyl, propyl, or n-butyl radical.

The esters of malic acid; in particular dialkyl esters of 2-hydroxy-butanedioic acid, are widely used in food industry and cosmetic industry because of their low toxicity, pleasant odor and good compatibility. For example, the diethyl ester of 2-hydroxy-butanedioic acid (diethyl malate) has a medium caramel scent and has been used as flavoring agent and cosmetic fragrance agent in food industry and cosmetic industry. The dibutyl ester of 2-hydroxy-butanedioic acid (diethyl malate) is used as a flavoring agent in food industry as well. The 2-hydroxy-butanedioic acid (malic acid) is a naturally occurring organic compound in various fruits and used as a food additive and preservative. The same is true of its diethyl ester and dibutyl ester.

Therefore, the silane-based crosslinkers according to the invention have many advantages compared to traditional crosslinkers. It is advantageous that the compounds having the general formula (I) releases only 2-hydroxy-butanedioic acid 1,4-dialkyl esters (dialkyl malate) (when R$^3$ is an alkyl) during crosslinking and are harmless for the environment and human and animal organisms. The ethyl and butyl esters of 2-hydroxy-butanedioic acid (diethyl malate and dibutyl malate) are even approved food additives.

Moreover, the released compound after crosslinking reaction according to the invention displays lower toxicity and an extremely low volatility, much lower than the hydrolysis products from all of the commercially available moisture-curing silane-based crosslinkers. Furthermore, the odors of the crosslinkers and the silicone rubber materials containing them are pleasant, in contrast to the foul-smelling oxime, and acetoxy silane-based crosslinkers. More importantly, the pleasant odor can be transmitted to the products using the crosslinker.

When n is 2 or 3 in the general formula (I), each R$^2$ is, independently of one another, selected from the group consisting of a hydrogen atom, a hydroxyl group, substituted or unsubstituted monovalent hydrocarbon radicals having from 1 to 18 carbon atoms, preferably from 1 to 8 carbon atoms, and alkoxy radicals having from 1 to 8 carbon atoms, preferably from 1 to 3 carbon atoms.

In preferred embodiments, R$^2$ is selected from monovalent hydrocarbon radicals having from 1 to 18 carbon atoms. More preferably, the hydrocarbon radical is selected from alkenyl, alkyl, or aryl radicals.

The alkenyl radical comprises at least one, two, or three C—C double bonds, preferably one C—C double bond. Alkenyl radicals can be substituted or unsubstituted. If they are substituted, the substituents are as defined above. The alkenyl radical comprises linear or branched hydrocarbon chains. In preferred embodiments, the alkenyl radical is selected from a vinyl radical or allyl radical. Examples of such silanes are vinyl-tri(diethyl malate)silane (formula 1), vinyl-tri(dibutyl malate)silane (formula 2), vinyl-tri(dimethyl malate)silane, allyl-tri(diethyl malate)silane, allyl-tri(dibutyl malate)silane and allyl-tri(dimethyl malate)silane, etc.

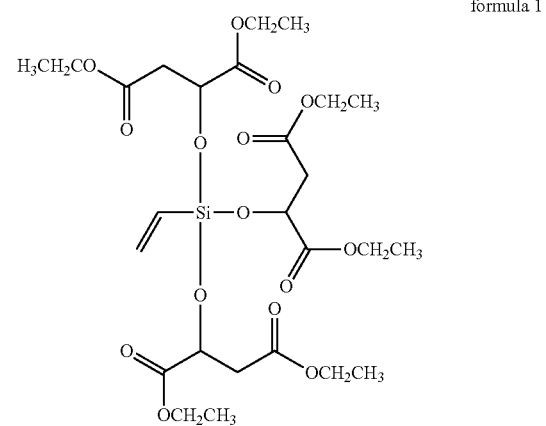

formula 1

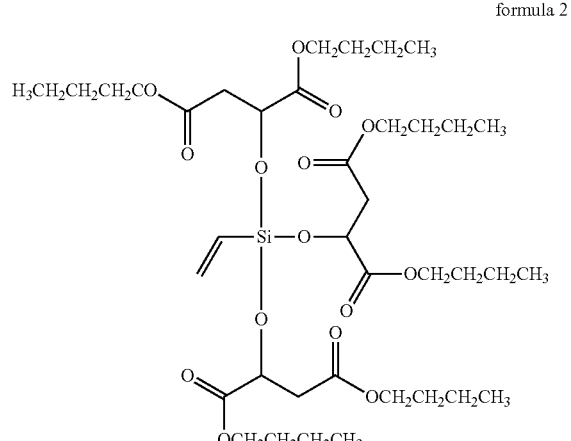

formula 2

The alkyl radical comprises linear or branched hydrocarbon chains, which comprise 1 to 18 carbon atoms, preferably 1 to 6 carbon atoms, more preferably 1 to 3 carbon atoms, and cyclic hydrocarbon such as cycloalkyl comprising from 5 to 20 carbon atoms, preferably 5 to 18 carbon atoms, more preferably 5 to 15 carbon atoms. Examples of such silanes are methyl-tri(diethyl malate)silane (formula 3), methyl-tri(dibutyl malate)silane (formula 4), methyl-tri(dimethyl malate)silane, methyl-tri(diethyl malate)silane, methyl-tri(dibutyl malate)silane, methyl-tri(dimethyl malate)silane, n-propyl-tri(diethyl malate)silane, n-propyl-tri(dibutyl malate)silane, n-propyl-tri(dimethyl malate)silane, i-propyl-tri(diethyl malate)silane, i-propyl-tri(dibutyl malate)silane and i-propyl-tri(dimethyl malate)silane, etc.

formula 3 formula 4

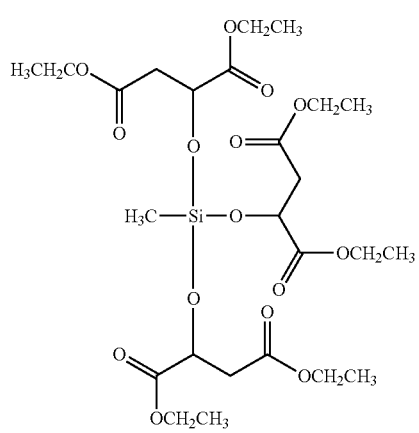

The aryl radical comprises aromatic hydrocarbon rings, which have at least five carbon atoms, and are preferably selected from phenyl and diphenyl groups. Examples of such silanes are phenyl-tri(diethyl malate)silane (formula 5), phenyl-tri(dibutyl malate)silane (formula 6), phenyl-tri(dimethyl malate)silane, diphenyl-tri(diethyl malate)silane, diphenyl-tri(dibutyl malate)silane and diphenyl-tri(dimethyl malate)silane, etc.

formula 5 formula 6

When n is 4 in the general formula (I), examples of such silanes are tetra(diethyl malate)silane (formula 7), tetra(dibutyl malate)silane (formula 8) and tetra(dimethyl malate)silane, etc.

formula 7

-continued

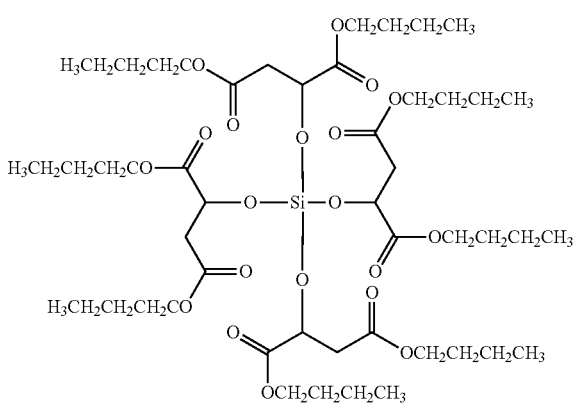

formula 8

The present invention also provides a method for preparing the silane compound according to the invention comprising a step of alcoholysis reaction of a silane having the general formula (III)

$$SiR^4{}_n(R^2)_{4-n} \quad (III)$$

with n equivalents of a compound having the general formula of HOCH(CH$_2$COOR$^3$)COXR$^3$ in solvent and using at least one tertiary amine as acid scavenger at room temperature. Each R$^4$ is same or different and is, independently of one another, selected from the group consisting of alkoxy radicals having from 1 to 4 carbon atoms, preferably a methoxy or an ethoxy radical, and Cl, preferably Cl, and R$^2$, n, R$^3$, and X are the same as defined for the general formulae (I) and (II) above.

Preferred solvents are diethyl ether, tetrahydrofuran, benzene, toluene, dichloromethane, chloroform, acetone, acetonitrile, 1,2-dichloroethane, 1,2-dimethoxy-ethane, N,N-dimethylformamide, 1,4-dioxane, and dimethyl sulfoxide, etc.

Preferred tertiary amines are triethylamine, tri(n-propyl) amine, tri(i-propyl)amine, tri(n-butyl)amine, tri(tert-butyl) amine, 1-methylimidazole, pyridine, quinuclidine, 4-dimethylaminopyridine, 2,6-lutidine, 3,5-lutidine, N,N-dimethylaniline, 1,4-dimethylpiperazine, 1,3,5-trimethylhexahydro-1,3,5-triazine, and N,N,N',N'-tetramethyldiaminomethane, etc.

The present invention is also directed to the use of the silane compounds according to the present invention as a crosslinker for a curable silicone compositions, preferably based on polyorganosiloxanes, or as an adhesion promoter for adhesives or sealants.

The present invention is also directed to crosslinkers comprising at least one silane compound having the general formula (I) according to the present invention. The crosslinker according to the invention may comprise one, two, or more compounds with the general formula (I) to allow the advantageous adjustment of the crosslinking rate.

The present invention is also directed to a curable composition comprising (A) at least one reaction product of
a) at least one polyorganosiloxane having at least one hydroxyl group, vinyl group, or hydrogen atom bound to a silicone atom; and
b) at least one silane compound having the general formula (I) according to the present invention; and
c) at least one catalyst.

The polyorganosiloxane is a polydiorganosiloxane, preferably a polydimethylsiloxane, which has at least one, preferably at least two terminal hydroxyl groups. In preferred embodiments, the polyorganosiloxane is selected from α,ω-dihydroxyl-terminated polyorganosiloxanes having the general formulation (IV)

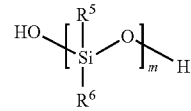

(IV)

wherein R$^5$ and R$^6$ are same or different and are, independently of one another, selected from the group consisting of substituted, preferably with at least one halogen atom or at least one functional group selected from cyano, amino, hydroxyl, or thiol groups, or unsubstituted cyclic, linear or branched alkyl or alkenyl radicals having from 1 to 18 carbon atoms or aryl radicals having from 6 to 18 carbon atoms, and m is 10 to 10000.

Especially preferred polyorganosiloxanes are α,ω-dihydroxyl-terminated polydimethylsiloxanes, α,ω-dihydroxyl-terminated polydiethylsiloxanes, α,ω-dihydroxyl-terminated polydivinylsiloxanes, α,ω-dihydroxyl-terminated polydiphenylsiloxanes, α,ω-dihydroxyl-terminated polymethylethylsiloxanes, α,ω-dihydroxyl-terminated polymethylvinylsiloxanes, α,ω-dihydroxyl-terminated polymethylphenylsiloxanes, α,ω-dihydroxyl-terminated polymethylchloromethylsiloxanes, α,ω-dihydroxyl-terminated polymethylchloropropylsiloxanes, α,ω-dihydroxyl-terminated polyethylvinylsiloxanes, α,ω-dihydroxyl-terminated polyethylphenylsiloxanes, α,ω-dihydroxyl-terminated polyvinylphenylsiloxanes, etc. These polysiloxanes having a kinematic viscosity of from 100 to 1000000 cSt at 25° C., preferably from 20000 to 100000 cSt at 25° C., more preferably from 40000 to 90000 cSt at 25° C. Mixtures comprising polydiorganosiloxanes having different viscosities may also be used.

The quantity of the polyorganosiloxanes in the composition described herein is from 30 to 90% by weight, more preferably 35 to 80% by weight, most preferably 40 to 70% by weight, based on the total weight of the curable composition.

The curable composition contains the silane of the general formula (I), preferably in an amount of 1 to 15% by weight, particularly preferably in an amount of 3 to 10% by weight, more preferably 3 to 6% by weight, based in each case on the total weight of the composition. If a mixture of a number of silanes of the general formula (I) is used, the quantitative data naturally refer to the total amount of silanes of the general formula (I) in the curable composition.

The curable compositions can contain the polyorganosiloxane, which has at least one hydroxyl group, vinyl group, or hydrogen atom bound to a silicon atom, and the silane of the general formula (I) as separate components. It is likewise possible, however, that these components are present in the form of a prepolymer. The prepolymer is a reaction product of the above-mentioned two components, at least one catalyst, and optionally at least one aminosilane. Suitable reactions are known and are also called endcapping. This can be carried out in the presence of at least one endcapping catalyst, whereby the catalyst is to mediate the endcapping selectively without simultaneously curing the polyorganosiloxane. Suitable catalysts are, for example, selected from the group consisting of acids, organic lithium compounds, for example, as described in EP 0564253 A1, amines, inorganic oxides, potassium acetate, titanium compounds such as organotitanium derivatives, titanium/amine combinations, tin compounds, carboxylic acid/amine combinations, and hydrosilylation catalysts such as platinum- and/or rhodium-containing catalysts.

If the polyorganosiloxane, which has at least one hydroxyl group bound to a silicon atom, and the silane of the general formula (I) are present as a prepolymer, thus the aforesaid quantitative data for polyorganosiloxane, on the one hand, and the silane, on the other, for the prepolymer are to be applied additively. The curable compositions, therefore, contain the prepolymer preferably in an amount of 32 to 97% by weight, particularly preferably in an amount of 44 to 66% by weight, based in each case on the total weight of the composition. If a mixture of a number of prepolymers is used, the quantitative data naturally refer to the total amount of prepolymers in the composition.

The reaction product may further comprise at least one aminosilane. Preferably, the aminosilane is selected from an aminosilane having the general formula (V)

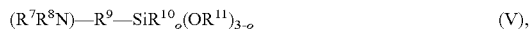

wherein
$R^7$ is selected from
  a hydrogen or
  substituted or unsubstituted alkyl, alkenyl, or alkynyl groups,
$R^8$ is selected from
  a hydrogen,
  substituted or unsubstituted alkyl, alkenyl, or alkynyl groups,
  substituted or unsubstituted cycloaliphatic groups or aryl groups,
  groups having the general formula of $-R^9-SiR^{10}{}_o(OR^{11})_{3-o}$, wherein $R^9$, $R^{10}$, $R^{11}$, and o are the same as defined below,
  groups having the general formula of $-(CH_2)_p-COOR^{12}$, wherein p is an integer from 2 to 10, particularly 2, and $R^{12}$ is selected from substituted or unsubstituted alkyl, alkenyl, or alkynyl groups, or a substituted or unsubstituted cycloaliphatic groups or aryl groups
$R^9$ is independently of one another selected from alkylene groups, optionally interrupted by a heteroatom,
$R^{10}$ is independently of one another selected from substituted or unsubstituted alkyl, alkenyl, or alkynyl groups, and
$R^{11}$ is independently of one another selected from
  substituted or unsubstituted alkyl, alkenyl, or alkynyl groups, acyl groups, or
  groups having the formula of $-CR^{13}{}_2COOR^{14}$, wherein $R^{13}$ is independently of one another selected from a hydrogen or substituted or unsubstituted alkyl, alkenyl, or alkynyl groups, or groups having the formula of $-CH_2COOR^3$, wherein $R^3$ has the meaning defined in the general formula (II); and $R^{14}$ is selected from substituted or unsubstituted alkyl, alkenyl, or alkynyl groups; and
o is 0, 1, or 2.

The aminosilane is preferably selected from 3-aminopropyltrimethoxysilane, 3-aminopropyltriethoxysilane, aminomethyltrimethoxysilane, aminomethyltriethoxysilane, 3-aminopropylmethyldiethoxysilane, (N-2-aminoethyl)-3-aminopropyltrimethoxysilane, (N-2-aminoethyl)-3-aminopropyltriethoxysilane, diethylenetriaminopropyltrimethoxysilane, phenylaminomethyltrimethoxysilane, (N-2-aminoethyl)-3-aminopropylmethyldimethoxysilane, 3-(N-phenylamino)propyl-trimethoxysilane, 3-piperazinylpropylmethyldimethoxysilane, 3-(N,N-dimethylaminopropyl)aminopropylmethyldimethoxysilane, tri[(3-triethoxysilyl)propyl]amine, tri[(3-trimethoxysilyl)propyl]amine, and the oligomers thereof, 3-(N,N-dimethylamino)propyltrimethoxysilane, 3-(N,N-dimethylamino)-propyltriethoxysilane, (N,N-dimethylamino)methyltrimethoxysilane, (N,N-dimethylamino)methyltriethoxysilane, bis(3-trimethoxysilyl)propylamine, bis(3-triethoxysilyl)propylamine, and mixtures thereof, particularly preferably of 3-aminopropyltrimethoxysilane, 3-aminopropyltriethoxysilane, aminomethyltrimethoxysilane, aminomethyltriethoxysilane, 3-(N,N-dimethylamino)propyltrimethoxysilane, 3-(N,N-dimethylamino)propyltriethoxysilane, (N,N-dimethylamino)methyltrimethoxysilane, (N,N-dimethylamino)methyltriethoxysilane, bis(3-trimethoxysilyl)propylamine, bis(3-triethoxysilyl)propylamine, and mixtures thereof. Malate-substituted aminosilanes can be also preferably used.

The reaction product may comprise the aminosilane, preferably in an amount of 0.05 to 4% by weight, more preferably in an amount of 0.1 to 2% by weight, particularly preferably in an amount of 0.2 to 2% by weight, based in each case on the total weight of the composition. If a mixture of a number of aminosilanes is used, the quantitative data naturally refer to the total amount of aminosilanes in the composition. The curable composition comprising the (A) at least one reaction product can further contain (B) at least one curing catalyst, preferably tin compound.

In preferred embodiments, this is an organotin compound or an inorganic tin salt. Tin in these tin compounds is preferably bivalent or tetravalent. The compound (B) is added to the composition particularly as a crosslinking catalyst. Suitable inorganic tin salts are, for example, tin(II) chloride and tin(IV) chloride. Organotin compounds (tin organyles) are used preferably as the tin compounds, however. Suitable organotin compounds are, for example, the 1,3-dicarbonyl compounds of bivalent or tetravalent tin, for example, the acetylacetonates such as di(n-butyl)tin(IV) di(acetylacetonate), di(n-octyl)tin(IV) di(acetylacetonate), (n-octyl)(n-butyl)tin(IV) di(acetylacetonate); the dialkyl tin (IV) dicarboxylates, for example, di-n-butyltin dilaurate, di-n-butyltin maleate, di-n-butyltin diacetate, di-n-octyltin dilaurate, di-n-octyltin diacetate, or the corresponding dialkoxylates, for example, di-n-butyltin dimethoxide; oxides of tetravalent tin, for example, dialkyltin oxides, such as, for example, di-n-butyltin oxide and di-n-octyltin oxide; and the tin(II) carboxylates such as tin(II) octoate or tin(II) phenolate.

Suitable furthermore are tin compounds of ethyl silicate, dimethyl maleate, diethyl maleate, dioctyl maleate, dimethyl phthalate, diethyl phthalate, dioctyl phthalate, such as, for example, di(n-butyl)tin(IV) di(methyl maleate), di(n-butyl)tin(IV) di(butyl maleate), di(n-octyl)tin(IV) di(methyl maleate), di(n-octyl)tin(IV) di(butyl maleate), di(n-octyl)tin (IV) di(isooctyl maleate); and di(n-butyl)tin(IV) sulfide, $(n-butyl)_2Sn(SCH_2COO)$, $(n-octyl)_2Sn(SCH_2COO)$, $(n-octyl)_2Sn(SCH_2CH_2COO)$, $(n-octyl)_2Sn(SCH_2CH_2COOCH_2CH_2OCOCH_2S)$, $(n-butyl)_2-Sn(SCH_2COO-i-C_8H_{17})_2$, $(n-octyl)_2Sn(SCH_2COO-i-C_8H_{17})_2$, and $(n-octyl)_2Sn(SCH_2COO-n-C_8H_{17})_2$.

Preferably, the tin compound is selected from 1,3-dicarbonyl compounds of bivalent or tetravalent tin, the dialkyltin (IV) dicarboxylates, the dialkyltin(IV) dialkoxylates, the dialkyltin(IV) oxides, the tin(II) carboxylates, and mixtures thereof.

Particularly preferably, the tin compound is a dialkyltin (IV) dicarboxylate, particularly di-n-butyltin dilaurate or di-n-octyltin dilaurate.

The curable composition can contain the tin compound preferably in an amount of 0.01 to 2% by weight, preferably in an amount of 0.05 to 2% by weight, particularly preferably in an amount of 0.1 to 0.5% by weight, based in each case on the total weight of the composition. If a mixture of a number of tin compounds is used, the quantitative data naturally refer to the total amount of tin compounds in the composition.

The compositions of, the invention crosslink in the presence of moisture and in so doing cure with the formation of Si—O—Si bonds.

If desired, the curable composition according to the invention may comprise other conventional additives in addition. The additives are catalysts, plasticizers, stabilizers, antioxidants, fillers, colorants, softeners, reactive diluents, drying agents, wetting agents, adhesion promoters, UV stabilizers, rheological aids, solvents and/or others.

Plasticizers and/or solvents may be used for reducing the viscosity of the curable composition according to the invention. Aliphatic or aromatic hydrocarbons, halogenated hydrocarbons, ketones, ethers, esters, ester alcohols, keto alcohols, keto ethers, keto esters, and ether esters are suitable as solvent.

The curable composition according to the invention may also contain hydrophilic plasticizers. These are used for improving the moisture absorption, and thus for enhancing the reactivity at low temperatures. Suitable as plasticizers, for example, are esters of abietic acid, adipic acid esters, azelaic acid esters, benzoic acid esters, butyric acid esters, acetic acid esters, esters of higher fatty acids containing approximately 8 to approximately 44 carbon atoms, esters of epoxidized fatty acids, fatty acid esters and fats, glycolic acid esters, phosphoric acid esters, phthalic acid esters, esters of linear or branched alcohols containing from 1 to 12 carbon atoms, propionic acid esters, sebacic acid esters, sulfonic acid esters, thiobutyric acid esters, trimellitic acid esters, citric acid esters, and esters based on nitrocellulose and polyvinyl acetate, and mixtures of two or more thereof.

Suitable among the phthalic acid esters, for example, are dioctyl phthalate, dibutyl phthalate, diisoundecyl phthalate, or butylbenzyl phthalate, and among the adipates are dioctyl adipate, diisodecyl adipate, diisodecyl succinate, dibutyl sebacate, or butyl oleate.

The curable composition according to the invention may also contain up to 20% by weight of customary adhesion promoters (tackifiers) and/or wetting agents based on the total weight of the composition. Suitable as adhesion promoters, for example, are silane compounds, resins, terpene oligomers, coumarone/indene resins, aliphatic petrochemical resins, and modified phenolic resins.

Preferred silane compounds are organosilanes containing having reactive amine groups, carboxylic acid groups, epoxy groups, or thiol groups, which may be same to the silanes having reactive groups according to the invention. Especially preferred samples of silane compounds are 3-aminopropyl-triethoxysilane, 3-aminopropyl-trimethoxysilane, 3-aminopropyl-tri(diethyl malate)silane, 3-aminopropyl-tri (dibutyl malate)silane, aminoethyl-aminopropyl-trimethoxysilane, butylaminopropyl-triethoxysilane, butylaminopropyl-trimethoxysilane, propylaminopropyl-triethoxysilane, propylaminopropyl-trimethoxysilane, N-cyclohexyl-3-aminopropyl-triethoxysilane, N-cyclohexyl-3-aminopropyl-trimethoxysilane, etc.

Suitable within the scope of the present invention, for example, are hydrocarbon resins which are obtained by polymerization of terpenes, primarily α- or β-pinene, dipentene, or limonene. The polymerization of these monomers generally takes place cationically with initiation with Friedel-Crafts catalysts. The terpene resins also include, for example, copolymers of terpenes and other monomers, for example styrene, α-methylstyrene, and isoprene. The stated resins are used, for example, as adhesion promoters for contact adhesives and coating materials. Likewise suited are terpene phenolic resins, which are produced by acid-catalyzed addition of phenols to terpenes or colophony. Terpene phenolic resins are soluble in most organic solvents and oils and miscible with other resins, waxes, and rubber. Likewise suitable as additives within the scope of the present invention are colophony resins and derivatives thereof, for example esters thereof.

Furthermore, the curable composition according to the invention may additionally contain up to about 7% by weight, in particular up to about 5% by weight, of antioxidants based on the total weight of the composition.

The curable composition according to the invention may contain up to about 2% by weight, preferably about 1% by weight, of UV stabilizers based on the total weight of the composition. The so-called hindered amine light stabilizers (HALS) are particularly suitable as UV stabilizers. Within the scope of the present invention, it is preferred to use a UV stabilizer which bears a silyl group and which is incorporated into the end product during crosslinking and curing. The products Lowilite 75 and Lowilite 77 (Great Lakes, US) are particularly suited for this purpose. In addition, benzotriazoles, benzophenones, benzoates, cyanoacrylates, acrylates, sterically hindered phenols, phosphorus, and/or sulfur may also be added.

It is often expedient to further stabilize the compositions according to the invention against penetrating moisture by use of drying agents in order to further extend the shelf life.

Such an improvement in the shelf life may be achieved, for example, by the use of drying agents. All compounds which react with water to form a group that is inert with respect to the reactive groups present in the composition, and which in the process preferably experience little change in their molecular weight, are suitable as drying agent. Furthermore, the reactivity of the drying agents with respect to moisture that has penetrated into the composition must be higher than the reactivity of the groups of the silyl group-bearing polymer according to the invention present in the composition.

Isocyanates, for example, are suitable as drying agent.

Silanes are advantageously used as drying agent. Examples are vinylsilanes such as 3-vinylpropyltriethoxysilane, oxime silanes such as methyl-O,O',O''-butan-2-one-trioximosilane or O,O',O'',O'''-butan-2-one-tetraoximosilane (CAS Nos. 022984-54-9 and 034206-40-1), or benzamidosilanes such as bis(N-methylbenzamido)methylethoxysilane (CAS No. 16230-35-6) or carbamatosilanes such as carbamatomethyltrimethoxysilane. However, the use of methyl-, ethyl-, or vinyltrimethoxysilane or tetramethoxy- or tetraethoxysilane is also possible. With regard to efficiency and cost, vinyltrimethoxysilane and tetraethoxysilane are particularly preferred here.

Likewise, suitable as drying agent are the above-mentioned reactive diluents, provided that they have a molecular weight ($M_n$) of less than about 5,000 g/mol and have end groups whose reactivity with respect to penetrated moisture is at least as high as, preferably higher than, the reactivity of the reactive groups of the silyl group-bearing polymer according to the invention.

Lastly, alkyl orthoformates or orthoacetates, for example methyl or ethyl orthoformate, methyl or ethyl orthoacetate, may also be used as drying agent.

The curable composition according to the invention generally contain about 0 to about 6% by weight of drying agent based on the total weight of the composition.

The curable composition according to the invention may additionally contain fillers. Suitable examples are chalk, lime powder, precipitated and/or pyrogenic silicic acid, zeolites, bentonites, magnesium carbonate, diatomaceous earth, alumina, clay, talc, titanium oxide, iron oxide, zinc oxide, sand, quartz, flint, mica, glass powder, and other ground mineral substances. In addition, organic fillers may also be used, in particular carbon black, graphite, wood fiber, wood flour, sawdust, cellulose, cotton, pulp, wood chips, chopped straw, and chaff. Moreover, short fibers such as glass fiber, glass filament, polyacrylonitrile, carbon fiber, Kevlar fiber, or also polyethylene fiber may be added. Powdered aluminum is likewise suitable as filler.

The pyrogenic and/or precipitated silicic acids advantageously have a BET surface area of 10 to 90 $m^2/g$. During use, they do not cause an additional increase in the viscosity of the composition according to the invention, but contribute to strengthening of the cured composition. It is likewise conceivable to use pyrogenic and/or precipitated silicic acids having a larger BET surface area, advantageously 100-250 $m^2/g$, in particular 110-170 $m^2/g$, as filler. Due to the larger BET surface area, the same effect, for example strengthening the cured composition, may be obtained at a lower weight fraction. Further substances may thus be used to improve the composition according to the invention with regard to other requirements.

For some applications, fillers are preferred which impart thixotropy to the compositions. Such fillers are also described as thixotropic agents, often also referred to as rheological aids, for example hydrogenated castor oil, fatty acid amides, or swellable plastics such as PVC. To allow them to be easily pressed out of a suitable dosing device (a tube, for example), such compositions have a viscosity of 3000 to 15,000 mPa·s, preferably 40,000 to 80,000 mPa·s, or also 50,000 to 60,000 mPa·s.

Furthermore, hollow spheres having a mineral shell or a plastic shell are suitable as filler. These may be, for example, hollow glass spheres which are commercially available under the trade name Glass Bubbles®. Hollow spheres based on plastic, for example Expancel® or Dualite®, are described in EP 0 520 426 B1, for example. These are composed of inorganic or organic substances, each having a diameter of 1 mm or less, preferably 500 µm or less.

Metal oxides are also useful as colorants, for example, titanium oxide as a white colorant.

The fillers are preferably used in a quantity of 1 to 80% by weight, based on the total weight of the composition.

The invention is further directed to the use of a composition according to the invention as adhesives, sealants, spray foam and coatings. The compositions find applications in the area of construction, electronic, communication, aerospace, cosmetic and medicine, etc., preferred application in the construction sector as a sealant or adhesive for joints in buildings and civil engineering projects, for metal, glass elements and windows and in sanitary installations.

In principle, in the present invention, all features mentioned in the context of the present text, in particular the embodiments, ranges of proportions, components and other features of the composition according to the invention and of the uses according to the invention shown as preferred and/or special can be implemented in all possible and not mutually exclusive combinations, with combinations of features shown as preferred and/or special also being regarded as preferred and/or special.

The following examples are used to explain the invention; however, the invention is not limited thereto.

EXAMPLE 1

Synthesis of Vinyl-Tri(Diethyl Malate)Silane (Formula 1)

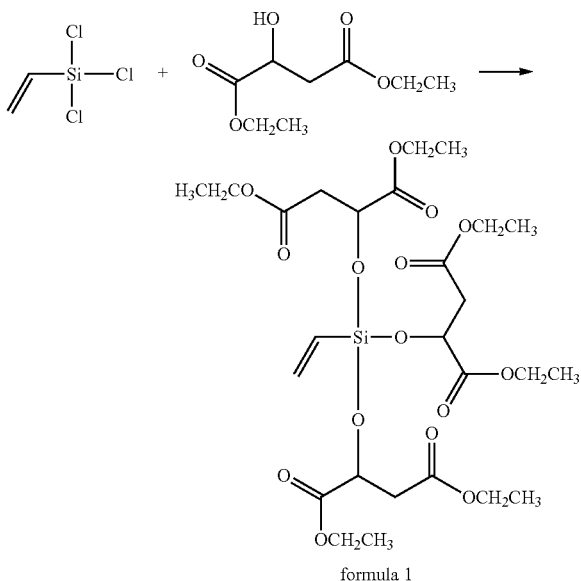

formula 1

In a 250 mL three-necked flask, vinyltrichlorosilane (3.23 g, 20 mmol) was added dropwise to the mixture of diethyl malate (11.41 g, 60 mmol), triethylamine (6.07 g, 60 mmol) in toluene (150 mL) under an atmosphere of argon at room temperature. After completion of the addition, the mixture was stirred overnight at room temperature, filtered and washed with toluene. The combined filtrates were distilled under vacuum to remove toluene and excess triethylamine. The product was afforded as a light yellow oil (11.6 g, yield: 93%).

EXAMPLE 2

Synthesis of Methyl-Tri(Diethyl Malate)Silane (Formula 3)

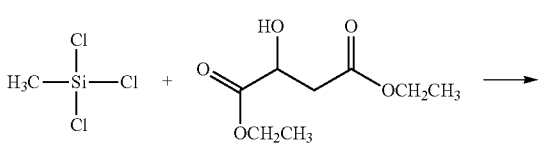

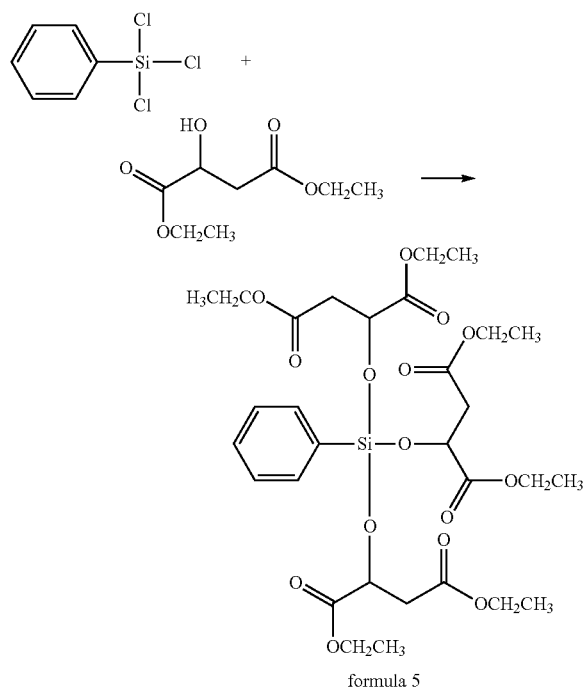

formula 3

In a 250 mL three-necked flask, methyltrichlorosilane (2.99 g, 20 mmol) was added dropwise to the mixture of diethyl malate (11.41 g, 60 mmol), triethylamine (6.07 g, 60 mmol) in toluene (120 mL) under an atmosphere of argon at room temperature. After completion of the addition, the mixture was stirred overnight at room temperature, filtered and washed with toluene. The combined filtrates were distilled under vacuum to remove toluene and excess triethylamine. The product was afforded as a light yellow oil (10.9 g, yield: 89%).

EXAMPLE 3

Synthesis of Phenyl-Tri(Diethyl Malate)Silane (Formula 5)

formula 5

In a 250 mL three-necked flask, phenyltrichlorosilane (4.23 g, 20 mmol) was added dropwise to the mixture of diethyl malate (11.41 g, 60 mmol), triethylamine (6.07 g, 60 mmol) in toluene (120 mL) under an atmosphere of argon at room temperature. After completion of the addition, the mixture was stirred overnight at room temperature, filtered and washed with toluene. The combined filtrates were distilled under vacuum to remove toluene and excess triethylamine. The product was afforded as a light yellow oil (11.9 g, yield: 89%).

EXAMPLES 4 TO 6 (E4 TO E6)

Preparation of Curable Compositions

Curable compositions were prepared according to the following formulation: 5 g of α,ω-dihydroxyl-terminated polydimethylsiloxane with viscosity 20000 mPa·s, 0.01 g of n-butyllithium (1.5M solutions in hexanes) and 0.02 g of dioctyltin dilaurate. In each case, 0.5 g of phenyl-tri(diethyl malate)silane, methyl-tri(diethyl malate)silane and vinyl-tri (diethyl malate)silane were added as crosslinkers for Examples 4, 5 and 6, respectively.

COMPARATIVE EXAMPLE 1 (C1)

A curable composition was prepared with 5 g of α,ω-dihydroxyl-terminated polydimethylsiloxane with viscosity 20000 mPa·s, 0.5 g of vinyltriethyllactatosilane, 0.1 g of n-butyllithium (1.5M solutions in hexanes) and 0.02 g of dioctyltin dilaurate.

After exposure to air, the crosslinking properties including skin over time (SOT) and tack free time (TFT) were determined. The results are shown in Table 1.

Test Method for Determining SOT and TFT

SOT: The aforementioned compositions were homogenized and applied in a frame (50×130×2 mm). Each mixture was evenly distributed so that the frame can be completely filled. A thin polymer film was thereby obtained. The time to form a skin (skin-over time/SOT) was determined for these compositions using a tool which has a rounded spatula at the tip (150×5 mm). The tip of the spatula was gently contacted with the surface of the polymer film every 1 to 5 minutes and removed carefully. The SOT was measured once no more residue of the formulation remains on the spatula when removing it from the surface of the polymer film. Then, the resulting string must be removed from the spatula without residue. The polymer film returned to its original shape. In examining the SOT a different part of the surface of the polymer film must be used every time. The test was performed at room temperature.

TFT: To determine surface tackiness from an adhesive sealing material, the aforementioned compositions were homogenized and applied in a frame (50×130×2 mm) in the same way as the SOT Determination. After 60 minutes, the tackiness of the surface was evaluated using a tool which has a rounded spatula at the tip (150×5 mm) by careful contact with the surface of the polymer film, TFT of "<60 min" indicates "not tacky" and of ">60 min" indicates "tacky (including slightly tacky)".

TABLE 1

| | skin over time (min) | tack free time (min) |
| --- | --- | --- |
| E4 | 33 | >60 |
| E5 | 32 | <60 |

TABLE 1-continued

| | skin over time (min) | tack free time (min) |
|---|---|---|
| E6 | 10 | <60 |
| C1 | 35 | <60 |

EXAMPLES 7 TO 9 (E7 TO E9)

Curable compositions were prepared according to the following formulation: 5 g of α,ω-dihydroxyl-terminated polydimethylsiloxane with viscosity 20000 mPa·s, 0.04 g of (3-aminopropyl)-trimethoxysilane, and 0.02 g dioctyltin dilaurate.

In each case, 0.5 g of phenyl-tri(diethyl malate)silane, methyl-tri(diethyl malate)silane and vinyl-tri(diethyl malate)silane were added as crosslinkers for Examples 7, 8 and 9, respectively.

COMPARATIVE EXAMPLES 2 TO 5 (C2 TO C5)

Comparative Example 2 (Alkoxy silicone): A curable composition was prepared according to the following formulation: 5 g of α,ω-dihydroxyl-terminated polydimethylsiloxane with viscosity 20000 mPa·s, 0.5 g of vinyltrimethoxysilane, 0.01 g of buthyllithium (1.6M in hexanes), and 0.02 g of dioctyltin carboxylate.

Comparative Example 3 (Acetoxy silicone): A curable composition was prepared according to the following formulation: 5 g of α,ω-dihydroxyl-terminated polydimethylsiloxane with viscosity 20000 mPa·s, 0.5 g of ethyltriacetoxysilane, and 0.02 g of dioctyltin dilaurate.

Comparative Example 4 (Lactate silicone): A curable composition was prepared according to the following formulation: 5 g of α,ω-dihydroxyl-terminated polydimethylsiloxane with viscosity 20000 mPa·s, 0.04 g of (3-aminopropyl)-triethoxysilane, 0.5 g of vinyltriethyllactatosilane, and 0.02 g of dioctyltin dilaurate.

Comparative Example 5 (Oxime silicone): A curable composition was prepared according to the following formulation: 5 g of α,ω-dihydroxyl-terminated polydimethylsiloxane with viscosity 80000 mPa·s, 0.18 g of a mixture of propan-2-one-O,O'(methoxyvinylsilandiyl)dioxime; propan-2-one-O-(dimethoxyvinylsilyl)oxime; propan-2-one-O,O',O"-(vinylsilantriyl)trioxime, 0.09 g of vinyltris(methylethylketoxime)silane, 0.27 g of a mixture of propan-2-one-O,O'(methoxyvinylsilandiyl)dioxime; propan-2-one-O-(dimethoxyvinylsilyl)oxime; propan-2-one-O,O',O"-(vinylsilantriyl)trioxime, with vinyltris(methylethylketoxime)silane with 0.01 g of dimethyltin dineodecanoate.

After exposure to air, the crosslinking properties including skin over time was determined according to the above-described methods. All measurements were carried out at room temperature. The results are shown in Table 2.

TABLE 2

| | Skin over time (min) |
|---|---|
| E7 | 60 |
| E8 | >120 |
| E9 | <5 |
| C2 | 15 |
| C3 | 15 |

TABLE 2-continued

| | Skin over time (min) |
|---|---|
| C4 | >120 |
| C5 | 15 |

The invention claimed is:

1. A silane compound having the general formula (I)

$$SiR^1{}_n(R^2)_{4-n} \qquad (I)$$

wherein each $R^1$ is same or different and is, independently of one another, selected from radicals having the general formula (II)

$$-OCH(CH_2COOR^3)COXR^3 \qquad (II)$$

wherein

X is O or N, and each $R^3$ is same or different and is, independently of one another, selected from the group consisting of substituted or unsubstituted, linear or branched alkyl radicals having from 1 to 22 carbon atoms, aryl radicals having from 6 to 16 carbon atoms, and cycloalkyl radicals having from 5 to 27 carbon atoms, where $R^3$ may contain at least one heteroatom selected from O, N, S and/or Si;

each $R^2$ is same or different and is, independently of one another, selected from the group consisting of a hydrogen atom, a hydroxyl group, substituted or unsubstituted monovalent hydrocarbon radicals having from 1 to 18 carbon atoms, and alkoxy radicals having from 1 to 8 carbon atoms; and n is 2, 3, or 4.

2. The silane compound according to claim 1, wherein $R^3$ is selected from the group consisting of linear or branched alkyl radicals having from 1 to 22 carbon atoms and cycloalkyl radicals having from 5 to 27 carbon atoms.

3. The silane compound according to claim 1, wherein $R^3$ is selected from the group consisting of a methyl, ethyl, propyl, and n-butyl radical.

4. The silane compound according to claim 1, wherein n is 3 or 4.

5. A method for preparing the silane compound having the general formula (I) according to claim 1, comprising:

providing a silane having the general formula (III)

$$SiR^4{}_n(R^2)_{4-n} \qquad (III);$$

providing a compound having the general formula of $$HOCH(CH_2COOR^3)COXR^3;$$

reacting the silane with n equivalents of the compound in an alcoholysis reaction in solvent and using at least one tertiary amine at room temperature, wherein each $R^4$ is same or different and is, independently of one another, selected from the group consisting of alkoxy radicals having from 1 to 4 carbon atoms and Cl;

$R^2$ and n are the same as defined for the general formula (I) in claim 1; and $R^3$ and X are the same as defined for the general formula (II) in claim 1.

6. The method according to claim 5, wherein the solvent is selected from the group consisting of diethyl ether, tetrahydrofuran, benzene, toluene, dichloromethane, chloroform, acetone, acetonitrile, 1,2-dichloroethane, 1,2-dimethoxy-ethane, N,N-dimethylformamide, 1,4-dioxane, dimethyl sulfoxide and combinations thereof.

7. The method according to claim 5, wherein the tertiary amine is selected from the group consisting of triethylamine, tri(n-propyl)amine, tri(i-propyl)amine, tri(n-butyl)amine, tri(tert-butyl)amine, 1-methylimidazole, pyridine, quinuclidine, 4-dimethylaminopyridine, 2,6-lutidine, 3,5-lutidine, N,N-dimethylaniline, 1,4-dimethylpiperazine, 1,3,5-trimethylhexahydro-1,3,5-triazine, N,N,N',N'-tetramethyldiaminomethane and combinations thereof.

8. A crosslinker for a curable silicone composition comprising at least one silane compound having the general formula (I) according to claim 1.

9. An adhesion promoter for adhesives or sealants comprising at least one silane compound having the general formula (I) according to claim 1.

10. A curable composition comprising (A) at least one reaction product of:
a) at least one polyorganosiloxane having at least one hydroxyl group, vinyl group, or hydrogen atom bound to a silicone atom;
b) at least one silane compound having the general formula (I) according to claim 1; and
c) at least one catalyst.

11. The curable composition according to claim 10, wherein (A) is the reaction product of a), b), c) and further d) at least one aminosilane.

12. The curable composition according to claim 10, wherein the polyorganosiloxane is a polydiorganosiloxane which has at least one, terminal hydroxyl group.

13. The curable composition according to claim 10, wherein the polyorganosiloxane is a polydiorganosiloxane which has at least two, terminal hydroxyl groups.

14. The curable composition according to claim 10, wherein the polyorganosiloxane is α,ω-dihydroxyl-terminated polyorganosiloxanes having the general formula (IV)

wherein $R^5$ and $R^6$ are same or different and are, independently of one another, selected from the group consisting of substituted or unsubstituted cyclic, linear or branched alkyl or alkenyl radicals having from 1 to 18 carbon atoms or aryl radicals having from 6 to 18 carbon atoms; and m is 10 to 10000.

15. The curable composition according to claim 10, further comprising (B) at least one curing catalyst.

16. An adhesive, sealant, spray foam and/or coating comprising the composition according to claim 10.

* * * * *

UNITED STATES PATENT AND TRADEMARK OFFICE
CERTIFICATE OF CORRECTION

PATENT NO.        : 10,590,151 B2
APPLICATION NO.   : 16/296361
DATED             : March 17, 2020
INVENTOR(S)       : Mejia et al.

Page 1 of 1

It is certified that error appears in the above-identified patent and that said Letters Patent is hereby corrected as shown below:

In the Claims

Column 20, Line 26: Change "Sand/or Si" to --S and/or Si--.

Signed and Sealed this
First Day of March, 2022

Drew Hirshfeld
*Performing the Functions and Duties of the*
*Under Secretary of Commerce for Intellectual Property and*
*Director of the United States Patent and Trademark Office*